United States Patent
Pham et al.

(10) Patent No.: US 6,475,971 B2
(45) Date of Patent: Nov. 5, 2002

(54) AZEOTROPE-LIKE COMPOSITION OF 1,2-DICHLORO-3,3,3-TRIFLUOROPROPENE AND HYDROGEN FLUORIDE COMPOSITION

(75) Inventors: Hang Thanh Pham, Erie County, NY (US); Rajiv Ratna Singh, Erie County, NY (US); Hsueh Sung Tung, Erie County, NY (US)

(73) Assignee: Honeywell International Inc., Morristown, NJ (US)

( * ) Notice: Subject to any disclaimer, the term of this patent is extended or adjusted under 35 U.S.C. 154(b) by 101 days.

(21) Appl. No.: 09/768,415

(22) Filed: Jan. 24, 2001

(65) Prior Publication Data

US 2002/0137645 A1 Sep. 26, 2002

(51) Int. Cl.$^7$ .................................................. C11D 7/30
(52) U.S. Cl. ...................... 510/408; 510/411; 510/412; 510/415
(58) Field of Search ................. 570/170, 178; 510/411, 412, 408, 415, 175, 176, 177; 8/610

(56) References Cited

U.S. PATENT DOCUMENTS

| | | | |
|---|---|---|---|
| 3,436,430 A | * | 4/1969 | Hall |
| 5,496,866 A | | 3/1996 | Sommerfeld et al. |
| 5,574,192 A | | 11/1996 | Van Der Puy et al. |
| 6,316,682 B1 | * | 11/2001 | Nakada et al. |

FOREIGN PATENT DOCUMENTS

| | | | | |
|---|---|---|---|---|
| JP | 402221389 A | * | 9/1990 | |
| JP | 402221496 A | * | 9/1990 | |
| JP | 402221702 A | * | 9/1990 | |
| JP | 402221962 A | * | 9/1990 | |

* cited by examiner

Primary Examiner—Gregory E. Webb
(74) Attorney, Agent, or Firm—Colleen Szuch

(57) ABSTRACT

The invention relates to azeotropic and azeotrope-like mixtures of 1,2-dichloro-3,3,3-trifluoropropene (HCFC-1223xd) and hydrogen fluoride, which are useful as intermediates in the production of HCFC-1223xd.

22 Claims, 1 Drawing Sheet

AZEOTROPE-LIKE COMPOSITION OF 1,2-DICHLORO-3,3,3-TRIFLUOROPROPENE AND HYDROGEN FLUORIDE COMPOSITION

FIELD OF THE INVENTION

The present invention pertains to azeotropic and azeotrope-like compositions of 1,2-dichloro-3,3,3-trifluoropropene (HCFC-1223xd) and hydrogen fluoride.

BACKGROUND

In recent years there has been universal concern that completely halogenated chlorofluorocarbons (CFC's) might be detrimental to the Earth's ozone layer. Consequently, there is a worldwide effort to use fluorine-substituted hydrocarbons that contain fewer or no chlorine substituents. In this regard, 1,1,1,3,3-pentafluoropropane, a hydrofluorocarbon (HFC) having zero ozone depletion potential, is being considered as a replacement for chlorofluorocarbons such as dichlorodifluoromethane in refrigeration systems and trichlorofluoromethane as a blowing agent. The production of HFC's, i.e. compounds containing only carbon, hydrogen and fluorine has been the subject of interest to provide environmentally desirable products for use as solvents, blowing agents, refrigerants, cleaning agents, aerosol propellants, heat transfer media, dielectrics, fire extinguishing compositions and power cycle working fluids. It is known in the art to produce fluorocarbons such as HFC's by reacting hydrogen fluoride with various hydrochlorocarbon compounds. Such HFC's are not only considered to be much more environmentally advantageous than hydrochlorofluorocarbons (HCFC's) or chlorofluorocarbons (CFC's) because they are not non-ozone depleting, but also they are also non-flammable, and non-toxic as compared to the chlorine containing compounds.

1,1,1,3,3-Pentafluoropropane (HFC-245fa) is well known in the art as described in U.S. Pat. Nos. 5,496,866 and 5,574,192, both of which are incorporated by reference herein in their entirety.

It has now been found that an intermediate in the production of substantially pure 1,1,1,3,3-pentafluoropropane, is an azeotropic or azeotrope-like mixture of 1,2-dichloro-3,3,3-trifluoropropene (HCFC-1223xd) and hydrogen fluoride. This intermediate, once formed, may thereafter be separated into its component parts by extraction techniques. The azeotropic and azeotrope-like compositions find use as anhydrous (non-aqueous) etchants for etching semiconductors in the electronics industry as well as compositions for removing surface oxidation from metals. After separation from HF, HCFC-1223xd may be used as a pharmaceutical intermediate.

SUMMARY OF THE INVENTION

In one embodiment, the invention provides an azeotropic composition consisting essentially of 1,2-dichloro-3,3,3-trifluoropropene and hydrogen fluoride.

The invention further provides an azeotropic or azeotrope-like composition consisting essentially of from about 1 to about 90 weight percent hydrogen fluoride and from about 10 to about 99 weight percent 1,2-dichloro-3,3,3-trifluoropropene, which composition has a boiling point of from about 26° C. to about 68° C. at a pressure of from about 24 psia to about 84 psia.

In another embodiment, the invention provides a method of forming an azeotropic or azeotrope-like composition, which method comprises blending from about 1 to about 90 weight percent hydrogen fluoride and from about 10 to about 99 weight percent of 1,2-dichloro-3,3,3-trifluoropropene, which composition has a boiling point of from about 26° C. to about 68° C. at a pressure of from about 24 psia to about 84 psia.

In still another embodiment, the invention provides a process for removing 1,2-dichloro-3,3,3-trifluoropropene from a mixture of 1,2-dichloro-3,3,3-trifluoropropene and at least one impurity, which process comprises adding hydrogen fluoride to the mixture in an amount sufficient to form an azeotropic or azeotrope-like composition of 1,2-dichloro-3,3,3-trifluoropropene and hydrogen fluoride, and thereafter separating the azeotropic composition from the impurity.

DETAILED DESCRIPTION OF THE PREFERRED EMBODIMENT

Figure 1:
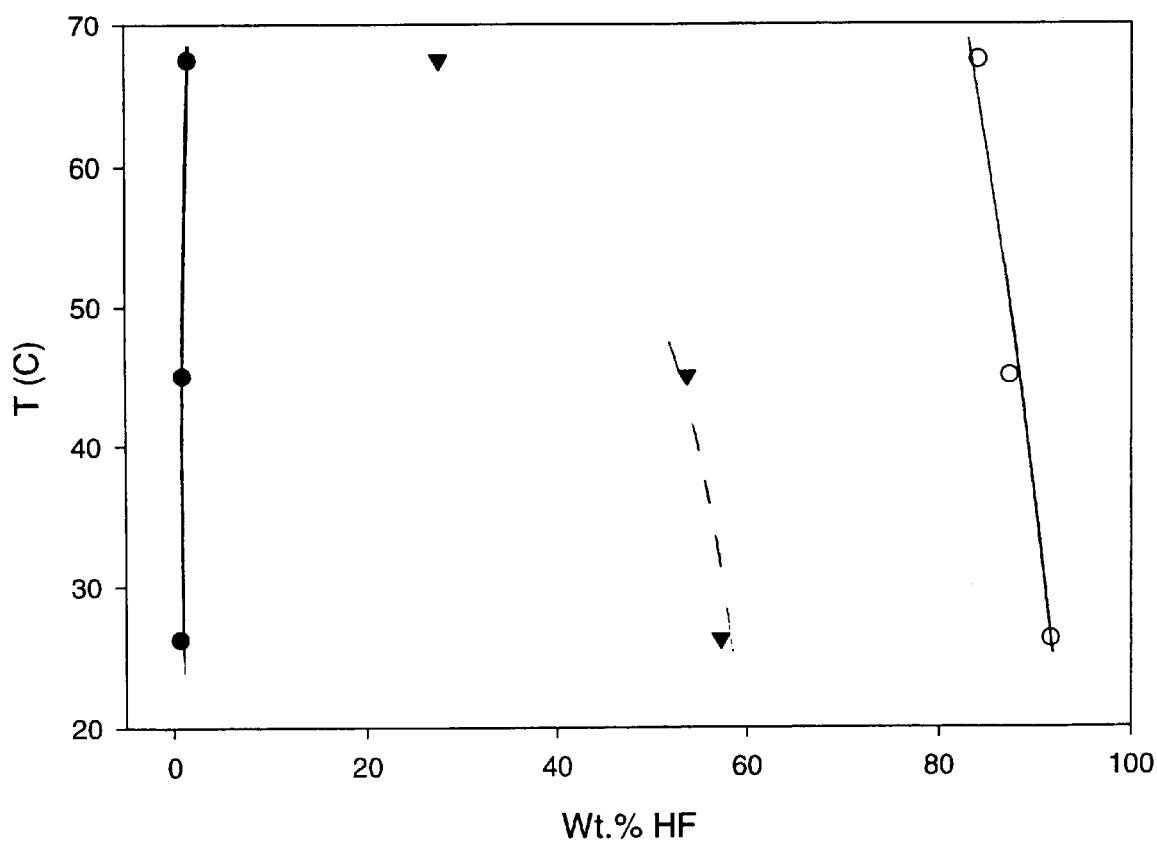
FIG. 1 shows a Vapor-Liquid-Liquid Equilibrium (VLLE) plot for HCFC-1223xd and HF.
Figure 1:
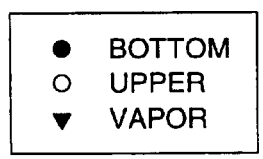

In a method of preparing HCFC-1223xd, precursor reagents are fluorinated with hydrogen fluoride. The reaction products of such precursors include HCFC-1223xd, unreacted HF and other by-products. Upon removal of the by-products, a binary azeotrope or azeotrope-like composition of HCFC-1223xd and HF is formed. This binary azeotrope or azeotrope-like composition is then available for separation into its component parts.

The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope-like composition means that the composition behaves like a true azeotrope in terms of its constant boiling characteristics and tendency not to fractionate upon boiling or evaporation. During boiling or evaporation, the liquid composition changes only slightly, if at all. This is in contrast with non-azeotrope-like compositions in which the liquid and vapor compositions change substantially during evaporation or condensation. One way to determine whether a candidate mixture is azeotrope-like within the meaning of this invention, is to distill a sample of it under conditions which would be expected to separate the mixture into its separate components. If the mixture is a non-azeotrope or non-azeotrope-like, the mixture will fractionate, i.e. separate into its various components with the lowest boiling component distilling off first, and so on. If the mixture is azeotrope-like, some finite amount of the first distillation cut will be obtained which contains all of the mixture components and which is constant boiling or behaves like a single substance. Another characteristic of azeotrope-like compositions is that there is a range of compositions containing the same components in varying proportions that are azeotrope-like. All such compositions are included by the term azeotrope-like as used herein. As an example, it is well known that at different pressures the composition of a given azeotrope will vary at least slightly as does the boiling point of the composition. Thus an azeotrope of two components represents a unique type of relationship but with a variable composition depending on the temperature and/or pressure. As is well known in the art, the boiling point of an azeotrope will vary with pressure.

As used herein, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition comprising effective amounts of hydrogen fluoride and HCFC-1223xd to form an azeotropic or azeotrope-like composition. By effective amount is meant an amount of each component which, when combined with the other component, results in the formation of an azeotrope or azeotrope-like mixture. The inventive compositions preferably are binary azeotropes that consist essentially of combinations of only hydrogen fluoride with HCFC-1223xd.

In the preferred embodiment, the inventive composition contains from about 1 to about 90 weight percent HF, preferably from about 10 weight percent to about 80 weight percent and most preferably from about 40 weight percent to about 60 weight percent. In the preferred embodiment, the inventive composition contains from about 10 to about 99 weight percent HCFC-1223xd, preferably from about 20 weight percent to about 90 weight percent and most preferably from about 40 weight percent to about 60 weight percent. The composition of the present invention has a boiling point of from about 26° C. to about 68° C. at a pressure of from about 24 psia to about 84 psia. An azeotropic or azeotrope-like composition having about 55±5 weight percent HF and about 45±5 weight percent HCFC-1223xd has been found to boil at about 26° C. and 23 psia. An azeotropic or azeotrope-like composition of about 50±5 weight percent HF and about 50±5 weight percent HCFC-1223xd has been found to boil at about 45° C. and 42 psia.

In another preferred embodiment of the invention, of HCFC-1223xd may be removed from a mixture containing of HCFC-1223xd and an impurity which may, for example, result from manufacturing steps in the preparation of HCFC-1223xd. This is done by adding hydrogen fluoride to a mixture of HCFC-1223xd and the impurity. Hydrogen fluoride is added to the mixture in an amount sufficient to form an azeotropic composition of HCFC-1223xd and hydrogen fluoride, and thereafter the azeotropic composition is separated from the impurity, for example by distillation, scrubbing, or other art recognized separating means. Preferably, the impurity itself does not form a close-boiling azeotropic mixture with HCFC-1223xd, hydrogen fluoride or a mixture of HCFC-1223xd and hydrogen fluoride. As used herein, the term close-boiling azeotropic mixture means an azeotropic mixture having a boiling point within 10° C. of the azeotropic mixture of the invention.

The following non-limiting examples serve to illustrate the invention.

EXAMPLE 1

50 g of 1,2-dichloro-3,3,3-trifluoropropene (HCFC-1223xd) is dissolved in 50 g of HF to form a heterogeneous mixture. The vapor pressure of the mixture at 26° C. is 23 psia.

EXAMPLE 2

55 g of 1,2-dichloro-3,3,3-trifluoropropene is dissolved in 45 g of HF to form a heterogeneous mixture. The vapor pressure of the mixture at 45° C. is 42 psia.

EXAMPLE 3

Vapor-Liquid-Liquid equilibrium was carried out at a temperature range of 26 to 68° C. for binary compositions consisting essentially of 1,2-dichloro-3,3,3-trifluoropropene and HF. The compositions of the upper liquid phase, the bottom phase and the vapor phase were sampled. The vapor pressure of the mixture was also recorded. The results are shown in Table 1. From Table 1 and Table 2, which reports the pure component vapor pressures, it is observed that the vapor pressure of the mixture is higher than the vapor pressure of each of the individual components. From this it is concluded that the mixture forms an azeotrope. The azeotropic composition is determined to be about 54 weight percent HF at 45° C. and about 57 weight percent HF at 26° C.

TABLE 1

| | | Composition (Wt. % HF) | | |
|---|---|---|---|---|
| Temperature (° C.) | Pressure (Psia) | Bottom Liquid Phase | Upper Liquid Phase | Vapor Phase |
| 26.2 | 23.6 | 0.65 | 91.7 | 57.3 |
| 45.0 | 42.2 | 0.95 | 87.4 | 53.7 |
| 67.6 | 83.7 | 1.56 | 84.0 | 27.7 |

TABLE 2

| Temperature (° C.) | Vapor Pressure of RF (Psia) | Vapor Pressure of HCFC-1223xd (Psia) |
|---|---|---|
| 26.2 | 18.4 | 6.0 |
| 45.0 | 34.0 | 12.1 |
| 67.6 | 66.2 | 23.7 |

What is claimed is:

1. An azeotropic composition consisting essentially of 1,2-dichloro-3,3,3-trifluoropropene and hydrogen fluoride.

2. An azeotropic or azeotrope-like composition consisting essentially of from about 1 to about 90 weight percent hydrogen fluoride and from about 10 to about 99 weight percent 1,2-dichloro-3,3,3-trifluoropropene, which composition has a boiling point of from about 26° C. to about 68° C. at a pressure of from about 23 psia to about 84 psia.

3. The composition of claim 2 which consists of hydrogen fluoride and 1,2-dichloro-3,3,3-trifluoropropene.

4. The composition of claim 2 wherein the hydrogen fluoride is present in an amount of from about 10 to about 80 weight percent.

5. The composition of claim 2 wherein the hydrogen fluoride is present in an amount of from about 40 to about 60 weight percent.

6. The composition of claim 2 having a boiling point of about 26° C. at a pressure of about 24 psia.

7. The composition of claim 2 having a boiling point of about 45° C. at a pressure of about 42 psia.

8. A method of forming an azeotropic or azeotrope-like composition which method consists essentially of blending from about 1 to about 90 weight percent hydrogen fluoride and from about 10 to about 99 weight percent 1,2-dichloro-3,3,3-trifluoropropene, which composition has a boiling point of from about 26° C. to about 68° C. at a pressure of from about 23 psia to about 84 psia.

9. The method of claim 8 wherein the composition consists of hydrogen fluoride and 1,2-dichloro-3,3,3-trifluoropropene.

10. The method of claim 8 wherein the hydrogen fluoride in present in an amount of from about 10 to about 80 weight percent.

11. The method of claim 8 wherein the hydrogen fluoride in present in an amount of from about 40 to about 60 weight percent.

12. The method of claim 8 wherein the composition has a boiling point of from about 26° C. at a pressure of about 24 psia.

13. The method of claim 8 wherein the composition has a boiling point of from about 45° C. at a pressure of about 42 psia.

14. A process for removing 1,2-dichloro-3,3,3-trifluoropropene from a mixture of 1,2-dichloro-3,3,3-trifluoropropene and at least one impurity, which process comprises adding hydrogen fluoride to the mixture in an amount sufficient to form an azeotropic or azeotrope-like composition of the 1,2-dichloro-3,3,3-trifluoropropene and the hydrogen fluoride, and thereafter separating the azeotropic composition from the impurity.

15. The process of claim 14 wherein the impurity does not form a close-boiling azeotropic mixture with 1,2-dichloro-3,3,3-trifluoropropene, hydrogen fluoride or a mixture of 1,2-dichloro-3,3,3-trifluoropropene and hydrogen fluoride.

16. The process of claim 14 wherein the impurity comprises a halocarbon.

17. The process of claim 14 wherein the impurity is miscible with 1,2-dichloro-3,3,3-trifluoropropene.

18. The process of claim 14 wherein the impurity is 1,1,1,3,3-pentachloropropane.

19. The process of claim 14 wherein the separating is conducted by distillation.

20. The process of claim 14 wherein the azeotropic composition consists essentially of from about 1 to about 90 weight percent hydrogen fluoride and from about 10 to about 99 weight percent 1,2-dichloro-3,3,3-trifluoropropene.

21. The process of claim 14 wherein the azeotropic composition consists essentially of from about 10 to about 80 weight percent hydrogen fluoride.

22. The process of claim 14 wherein the azeotropic composition consists essentially of from about 40 to about 60 weight percent hydrogen fluoride.

* * * * *

UNITED STATES PATENT AND TRADEMARK OFFICE
Certificate

Patent No. 6,475,971 B2    Patented: November 5, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Hang Thanh Pham, Erie County, NY; Rajiv Ratna Singh, Erie County, NY; Hsueh Sung Tung, Erie County, NY; and Daniel Christopher Merkel, West Seneca, NY.

Signed and Sealed this Thirty-first Day of January 2006.

YOGENDRA N. GUPTA
*Supervisory Patent Examiner*
Art Unit 1751